US00PP19540P2

(12) United States Plant Patent
Hilder et al.

(10) Patent No.: US PP19,540 P2
(45) Date of Patent: Dec. 2, 2008

(54) ***ALLAMANDA* PLANT NAMED 'CARAMEL BLUSH'**

(50) Latin Name: *Allamanda carthartica*
Varietal Denomination: Caramel Blush

(76) Inventors: Ronald Richard Hilder, 83 Allens Road, Upper Stone via Ingham, Queensland (AU), 4850; Gloria Ellen May Hilder, 83 Allens Road, Upper Stone via Ingham, Queensland (AU), 4850

( * ) Notice: Subject to any disclaimer, the term of this patent is extended or adjusted under 35 U.S.C. 154(b) by 0 days.

(21) Appl. No.: 11/804,610

(22) Filed: May 19, 2007

(51) Int. Cl.
*A01H 5/00* (2006.01)

(52) U.S. Cl. ..... Plt./263.1

(58) Field of Classification Search ..... Plt./263.1
See application file for complete search history.

(56) References Cited

PUBLICATIONS

UPOV–ROM search for cultivar Caramel Blush PBR 20051871 p. 1.*

* cited by examiner

*Primary Examiner*—Annette H Para

(57) ABSTRACT

A new cultivar of *Allamanda* plant named 'Caramel Blush' that is characterized by flowering during low light conditions and large yellow flowers with a yellow-orange center.

1 Drawing Sheet

Botanical classification: *Allamanda carthartica.*
Variety denomination: 'Caramel Blush'.

BACKGROUND OF THE INVENTION

The present invention relates to a new and distinct cultivar of *Allamanda* plant botanically known as *Allamanda carthartica* and hereinafter referred to by the cultivar name 'Caramel Blush'.

The cultivar 'Caramel Blush' was discovered and selected in 2002 as a single plant in Upper Stone via Ingram, Queensland, Australia. 'Caramel Blush' was discovered growing in a bed of unnamed *Allamanda* cultivars. The exact parents are unknown.

Asexual reproduction of the new cultivar 'Caramel Blush' first occurred by terminal cuttings in 2003 in De Lier, The Netherlands. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Allamanda* cultivar 'Caramel Blush'. These traits in combination distinguish 'Caramel Blush' as a new and distinct cultivar apart from other existing known varieties of *Allamanda.*

1. *Allamanda* 'Caramel Blush' exhibits flowering during low light conditions.
2. *Allamanda* 'Caramel Blush' exhibits large yellow flowers with a yellow-orange center.

The closest comparison cultivars are plants of the *Allamanda cathartica* species. 'Caramel Blush' is distinguishable from plants of the species by the following characteristics:

1. 'Caramel Blush' has flowers with a yellow-orange center. Plants of the *Allamanda* species do not have a yellow-orange center.
2. 'Caramel Blush' exhibits larger flowers.
3. 'Caramel Blush' flowers readily under low light conditions.

Plants of the new *Allamanda* can be compared to plants of the cultivar 'BCT9810ALL' (U.S. Plant Pat. No. 13,435). 'Caramel Blush' differs from 'BCT9810ALL' in the following characteristics:

1. 'Caramel Blush' has single flowers with a yellow-orange center. 'BCT9810ALL' has double yellow flowers.

BRIEF DESCRIPTION OF THE DRAWING

The accompanying photograph illustrates the distinguishing traits of *Allamanda* 'Caramel Blush'. The plant in the photograph shows an overall view of a 2 year old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Allamanda* cultivar named 'Caramel Blush'. Data was collected in De Kwakel, The Netherlands from 2 year old glass greenhouse grown plants in 15 cm. diameter containers. The time of year was Winter and the temperature range was 20–22 degrees Centigrade during the day and 20–22 degrees Centigrade at night. The light level was natural outdoor light. Color determinations are in accordance with The Royal Horticultural Society Colour Chart 2001 edition, except where general color terms of ordinary dictionary significance are used. The growing requirements are similar to the species. 'Caramel Blush' has not been tested under all possible conditions and phenotypic differences may be observed with variations in environmental, climatic, and cultural conditions, however, without any variance in genotype.

Botanical classification: *Allamanda carthartica* 'Caramel Blush'.
Use: Ornamental Annual.
Parentage: The exact parents of 'Caramel Blush' are unknown.
Vigor: Moderate to high.
Growth habit: Irregular upright.
Plant shape: Broad upright.
Suitable container size: 15 cm. pots.
Height: 84.5 cm. in height.
Width: 83.5 cm. in width.
Low temperature tolerance: USDA Zone 10.
High temperature tolerance: 40° Centigrade.
Propagation: Terminal cuttings.
Time to initiate roots: 56 days to initiate roots at 24–25° Centigrade.
Time to produce a rooted cutting or liner: 84 days at 24–25° Centigrade.
Growth rate: Approximately 15 cm. per month in spring.
Root system: Moderately fibrous.
Stem:
*Branching habit.*—Moderately branched.
*Pinching.*—Required.
*Number of lateral branches.*—Average 7 branches.
*Lateral branch length.*—34.2 cm.
*Lateral branch diameter.*—3.5 mm.
*Internode length.*—8.1 cm.
*Stem shape.*—Rounded and moderately glossy.
*Stem aspect.*—Rounded.
*Stem strength.*—Moderately strong.
*Stem color.*—Young twigs, 144A; older bark 197B to 197D.
*Pubescence.*—Lateral branches covered densely with short bristly hairs, 0.75 mm in length, 157D.
Foliage:
*Texture.*—Only slightly glossy.
*Leaf arrangement.*—In whorls of 4.
*Compound or single.*—Single.
*Quantity of leaves.*—Average 20; 5 whorls.
*Leaf shape.*—Elliptic to obovate and ovate.
*Leaf apex.*—Abruptly acute.
*Leaf base.*—Obtuse.
*Leaf length.*—8.4 cm. in length.
*Leaf width.*—4.8 cm. in width.
*Pubescence.*—Upper sides covered moderately and under sides densely with 0.75 mm hairs, 157D.
*Leaf margin.*—Entire, moderately undulate.
*Young leaf color* (*lower surface*).—145B.
*Young leaf color* (*upper surface*).—143A.
*Mature leaf color* (*lower surface*).—In between 145B and 146D.
*Mature leaf color* (*upper surface*).—137A.
*Vein color* (*under surface*).—145B.
*Vein color* (*upper surface*).—147C.
*Venation pattern.*—Pinnate.
*Leaf attachment.*—Petiolate.
*Petiole dimensions.*—2 mm. in length, and 3 mm. in width.
*Petiole color.*—145B.
Flower:
*Inflorescence arrangement.*—In terminal and axillary pairs.
*Flowering habit.*—Continuous.
*Quantity of flowers per inflorescence.*—Average 2.
*Flower type.*—Single.
*Quantity of flowers per lateral stem.*—Average 4.
*Quantity of flower buds per lateral stem.*—Average 4.
*Quantity of flowers and buds per plant.*—20.
*Natural flowering season.*—Summer.
*Fragrance.*—None.
*Rate of flower opening.*—Flowers in a cyme do not open simultaneously.
*Flower bud length.*—5 mm. in length.
*Flower bud diameter.*—3 mm. in diameter.
*Flower bud shape.*—Ovate.
*Bud color.*—144A.
*Rate of bud opening.*—10 days.
*Flower aspect.*—Outward.
*Flower shape.*—Funnelform.
*Flower dimensions.*—7.4 cm. in diameter and 8.1 cm. in height.
*Flower longevity.*—A few days.
*Petal appearance.*—Upper (inner) side dull, onder (outer) side moderately glossy.
*Petal texture.*—Slightly leathery and smooth.
*Number of petals.*—5.
*Fused or unfused.*—Only the lower 70% are fused.
*Petal arrangement.*—Fused into a funnelform.
*Petal shape.*—Spathulate, upper 30% orbicular.
*Petal margin.*—Entire, lower 70% fused.
*Petal apex.*—Retuse.
*Petal length.*—9.9 cm. in length.
*Petal width.*—3.7 cm.
*Petal color when opening* (*upper side*).—Lower part 4C; upper wide part 22A to 22C to 34C to 34D, free part 4A tinged 22B to 22D.
*Petal color when opening* (*under side*).—Lower part 154A to 154B to 1B; upper wide part 10C to 24C to 24D, free part 4B to 4C tinged 22A to 22B.
*Petal color fully opened* (*upper side*).—Lower part 4C; upper wide part 22A to 22C to 34C to 34D, free part 4A tinged 22B to 22D.
*Petal color fully opened* (*under side*).—Lower part 154A to 154B to 1B; upper wide part 10C to 24C to 24D, free part 4B to 5C tinged 22A to 22B.
*Petal color fading to.*—Not fading.
*Self-cleaning or persistent.*—Self-cleaning.
Sepals:
*Number of sepals.*—Average 5.
*Sepal aspect.*—Rotate, fused at the base.
*Sepal shape.*—Oblanceolate.
*Sepal margin.*—Entire.
*Sepal apex.*—Acute.
*Sepal base.*—Fused cuneate.
*Sepal surface.*—Glossy and pubescent, hairs 0.5 mm, colored 157D.
*Sepal dimensions.*—2.1 cm. in length and 9 mm. in width.
*Young sepal color* (*upper side*).—145A.
*Young sepal color* (*under side*).—145B.
*Mature sepal color* (*upper side*).—144B, base 145C.
*Mature sepal color* (*under side*).—145B.
Calyx:
*Calyx shape.*—Rotate.
*Calyx dimensions.*—1.7 cm. in length and 2.8 cm. in diameter.
Pedicels:
*Pedicel length.*—Average 8 mm.

*Pedicel diameter.*—Average 3 mm.
*Pedicel angle.*—Average 35°.
*Pedicel strength.*—Moderately strong.
*Pedicel color.*—144B.

Reproduction organs:

*Stamen number.*—Average 5.
*Anther shape.*—Narrow triangular.
*Anther size.*—Average 5 mm.
*Anther color.*—161B.
*Amount of pollen.*—Very low.
*Pollen color.*—161B to 161C.
*Pistil number.*—Average 1.
*Pistil length.*—Average 3.4 cm. in length.
*Stigma shape.*—Capitate.
*Stigma color.*—145B.
*Style length.*—3.1 cm.
*Style color.*—150D.
*Ovary color.*—154C to 154D.

Disease and pest resistance: Plants of the new cultivar have not been observed for disease and pest resistance.

What is claimed is:

1. A new and distinct variety of *Allamanda* plant named 'Caramel Blush' as described and illustrated.

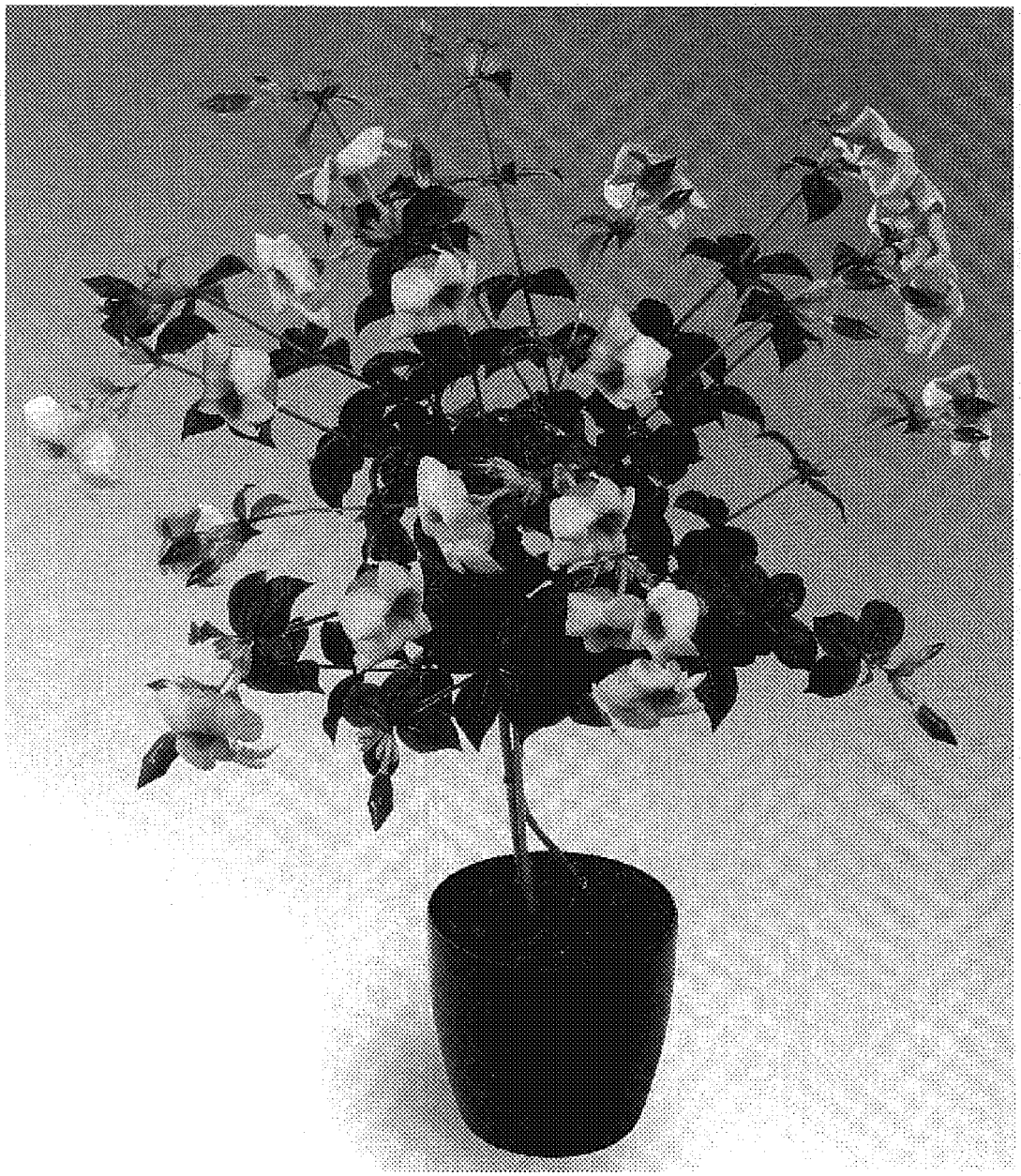

* * * * *